US009999751B2

(12) United States Patent
Pacheco et al.

(10) Patent No.: US 9,999,751 B2
(45) Date of Patent: Jun. 19, 2018

(54) ADJUSTABLE NOSE CONE FOR A CATHETER POSITIONING SYSTEM

(71) Applicant: Catheter Precision, Inc., Ledgewood, NJ (US)

(72) Inventors: Robert Pacheco, Bayside, NY (US); Steve Foley, Kerrville, TX (US); David Jenkins, Budd Lake, NJ (US); Brandon D. Guarino, Howard Beach, NY (US)

(73) Assignee: CATHETER PRECISION, INC., Ledgewood, NJ (US)

( * ) Notice: Subject to any disclaimer, the term of this patent is extended or adjusted under 35 U.S.C. 154(b) by 841 days.

(21) Appl. No.: 14/478,711

(22) Filed: Sep. 5, 2014

(65) Prior Publication Data

US 2015/0073339 A1 Mar. 12, 2015

Related U.S. Application Data

(60) Provisional application No. 61/874,439, filed on Sep. 6, 2013.

(51) Int. Cl.
*A61M 25/01* (2006.01)
*A61B 17/00* (2006.01)
(Continued)

(52) U.S. Cl.
CPC ......... *A61M 25/0113* (2013.01); *A61B 34/30* (2016.02); *A61B 2017/00477* (2013.01); *A61B 2034/301* (2016.02); *A61B 2090/0811* (2016.02)

(58) Field of Classification Search
CPC .... A61M 25/0113; A61B 34/30; A61B 34/70; A61B 2034/301
See application file for complete search history.

(56) References Cited

U.S. PATENT DOCUMENTS

| 4,549,538 A | 10/1985 | Schadrack, III et al. |
| 4,721,123 A | 1/1988 | Cosentino et al. |

(Continued)

FOREIGN PATENT DOCUMENTS

| JP | 2007527296 A | 9/2007 |
| WO | 2005087128 A1 | 9/2005 |

(Continued)

OTHER PUBLICATIONS

WIPO, International Preliminary Report on Patentability: PCT/US2006/027024; dated Jan. 16, 2008; 8pgs.

(Continued)

*Primary Examiner* — Laura Bouchelle
(74) *Attorney, Agent, or Firm* — The Marbury Law Group, PLLC

(57) ABSTRACT

Various embodiments enable an introducer for a catheter to be rotated around an axis and/or traversed backward and/or forward along the axis. In various embodiments, positioning of an introducer may be enabled by an introducer support configured to be rotated around an axis and/or extended or retracted along the axis. The introducer may be manually operated and/or operated by motors in a nose cone of a catheter positioning system. In various embodiments, a portion of the introducer support may be configured to flex. In other embodiment, positioning of an introducer may be enabled by an adjustable nose cone of a catheter positioning system.

4 Claims, 11 Drawing Sheets

(51) Int. Cl.
*A61B 34/30* (2016.01)
*A61B 90/00* (2016.01)

(56) References Cited

U.S. PATENT DOCUMENTS

| | | | |
|---|---|---|---|
| 5,226,892 A | 7/1993 | Boswell | |
| 5,328,486 A * | 7/1994 | Woodruff | A61M 5/31555 |
| | | | 604/207 |
| 5,458,602 A * | 10/1995 | Goble | A61B 17/1714 |
| | | | 606/96 |
| 5,644,551 A | 7/1997 | Carmichael et al. | |
| 5,649,956 A | 7/1997 | Jensen et al. | |
| 5,682,890 A | 11/1997 | Kormos et al. | |
| 5,810,880 A | 9/1998 | Jensen et al. | |
| 5,814,038 A | 9/1998 | Jensen et al. | |
| 5,827,313 A * | 10/1998 | Ream | A61B 5/0066 |
| | | | 600/471 |
| 5,855,583 A | 1/1999 | Wang et al. | |
| 6,007,550 A | 12/1999 | Wang et al. | |
| 6,063,095 A | 5/2000 | Wang et al. | |
| 6,074,395 A * | 6/2000 | Trott | A61B 17/068 |
| | | | 606/104 |
| 6,080,181 A | 6/2000 | Jensen et al. | |
| 6,096,004 A | 8/2000 | Meglan et al. | |
| 6,132,368 A | 10/2000 | Cooper | |
| 6,171,234 B1 | 1/2001 | White et al. | |
| 6,171,277 B1 | 1/2001 | Ponzi | |
| 6,200,315 B1 | 3/2001 | Gaiser et al. | |
| 6,346,072 B1 | 2/2002 | Cooper | |
| 6,396,232 B2 | 5/2002 | Haanpaa et al. | |
| 6,398,755 B1 | 6/2002 | Belef et al. | |
| 6,413,264 B1 | 7/2002 | Jensen et al. | |
| 6,445,984 B1 | 9/2002 | Kellogg | |
| 6,461,372 B1 | 10/2002 | Jensen et al. | |
| 6,527,782 B2 | 3/2003 | Hogg et al. | |
| 6,620,174 B2 | 9/2003 | Jensen et al. | |
| 6,726,675 B1 | 4/2004 | Beyar | |
| 6,788,999 B2 | 9/2004 | Green | |
| 6,850,817 B1 | 2/2005 | Green | |
| 6,963,792 B1 | 11/2005 | Green | |
| 6,974,465 B2 | 12/2005 | Belef et al. | |
| 6,999,852 B2 | 2/2006 | Green | |
| 7,006,895 B2 | 2/2006 | Green | |
| 7,090,683 B2 | 8/2006 | Brock et al. | |
| 7,118,582 B1 | 10/2006 | Wang et al. | |
| 7,169,141 B2 | 1/2007 | Brock et al. | |
| 7,204,844 B2 | 4/2007 | Jensen et al. | |
| 7,214,230 B2 | 5/2007 | Brock et al. | |
| 7,276,044 B2 | 10/2007 | Ferry et al. | |
| 7,314,230 B2 | 1/2008 | Kumagai et al. | |
| 7,331,967 B2 | 2/2008 | Lee et al. | |
| 7,357,774 B2 | 4/2008 | Cooper | |
| 7,371,210 B2 | 5/2008 | Brock et al. | |
| 7,377,906 B2 | 5/2008 | Selkee | |
| 7,537,570 B2 | 5/2009 | Kastelein | |
| 7,604,645 B2 * | 10/2009 | Barzell | A61B 8/12 |
| | | | 600/429 |
| 7,630,752 B2 | 12/2009 | Viswanathan | |
| 7,648,513 B2 | 1/2010 | Green et al. | |
| 7,758,564 B2 | 7/2010 | Long et al. | |
| 8,046,049 B2 | 10/2011 | Govari et al. | |
| 8,672,880 B2 | 3/2014 | Cohen et al. | |
| 2001/0053879 A1 | 12/2001 | Mills et al. | |
| 2002/0042620 A1 | 4/2002 | Julian et al. | |
| 2002/0072704 A1 | 6/2002 | Mansouri-Ruiz | |
| 2002/0120254 A1 | 8/2002 | Julian et al. | |
| 2002/0177789 A1 | 11/2002 | Ferry et al. | |
| 2002/0183723 A1 | 12/2002 | Belef et al. | |
| 2004/0077942 A1 | 4/2004 | Hall et al. | |
| 2004/0254566 A1 | 12/2004 | Plicchi et al. | |
| 2005/0038412 A1 | 2/2005 | Rabiner et al. | |
| 2005/0065435 A1 | 3/2005 | Rauch et al. | |
| 2005/0113719 A1 | 5/2005 | Saadat | |
| 2005/0203382 A1 | 9/2005 | Govari et al. | |
| 2005/0209614 A1 | 9/2005 | Fenter et al. | |
| 2005/0222554 A1 | 10/2005 | Wallace et al. | |
| 2005/0228440 A1 | 10/2005 | Brock et al. | |
| 2005/0277874 A1 | 12/2005 | Selkee | |
| 2005/0283140 A1 | 12/2005 | Jensen et al. | |
| 2006/0009735 A1 | 1/2006 | Viswanathan et al. | |
| 2006/0041181 A1 | 2/2006 | Viswanathan et al. | |
| 2006/0084911 A1 | 4/2006 | Belef et al. | |
| 2006/0084945 A1 | 4/2006 | Moll et al. | |
| 2006/0095022 A1 | 5/2006 | Moll et al. | |
| 2006/0161136 A1 | 7/2006 | Anderson et al. | |
| 2006/0161137 A1 | 7/2006 | Orban et al. | |
| 2006/0161138 A1 | 7/2006 | Orban et al. | |
| 2006/0167441 A1 | 7/2006 | Wang et al. | |
| 2006/0178559 A1 | 8/2006 | Kumar et al. | |
| 2006/0229587 A1 | 10/2006 | Beyar | |
| 2006/0235436 A1 | 10/2006 | Anderson et al. | |
| 2006/0270915 A1 | 11/2006 | Ritter et al. | |
| 2006/0293643 A1 | 12/2006 | Wallace et al. | |
| 2007/0012135 A1 | 1/2007 | Tierney et al. | |
| 2007/0016174 A1 | 1/2007 | Cohen et al. | |
| 2007/0019330 A1 | 1/2007 | Wolfersberger | |
| 2007/0021776 A1 | 1/2007 | Jensen et al. | |
| 2007/0043338 A1 | 2/2007 | Moll et al. | |
| 2007/0043455 A1 | 2/2007 | Viswanathan et al. | |
| 2007/0149946 A1 | 6/2007 | Viswanathan et al. | |
| 2007/0233044 A1 | 10/2007 | Wallace et al. | |
| 2007/0239172 A1 | 10/2007 | Lee et al. | |
| 2007/0250073 A1 | 10/2007 | Brock et al. | |
| 2007/0250074 A1 | 10/2007 | Brock et al. | |
| 2007/0260115 A1 | 11/2007 | Brock et al. | |
| 2007/0276423 A1 | 11/2007 | Green | |
| 2007/0283263 A1 | 12/2007 | Zawde et al. | |
| 2007/0299479 A1 | 12/2007 | Saksena | |
| 2008/0009791 A1 | 1/2008 | Cohen et al. | |
| 2008/0039869 A1 | 2/2008 | Mills et al. | |
| 2008/0045892 A1 | 2/2008 | Ferry et al. | |
| 2008/0059598 A1 | 3/2008 | Garibaldi et al. | |
| 2008/0119824 A1 | 5/2008 | Weitzner et al. | |
| 2008/0119872 A1 | 5/2008 | Brock et al. | |
| 2008/0125793 A1 | 5/2008 | Brock et al. | |
| 2008/0125794 A1 | 5/2008 | Brock et al. | |
| 2008/0140087 A1 | 6/2008 | Barbagli | |
| 2008/0147091 A1 | 6/2008 | Cooper | |
| 2008/0183136 A1 | 7/2008 | Lenker et al. | |
| 2008/0215065 A1 | 9/2008 | Wang et al. | |
| 2008/0245946 A1 | 10/2008 | Yu | |
| 2008/0249536 A1 | 10/2008 | Stahler et al. | |
| 2008/0300592 A1 | 12/2008 | Weitzner et al. | |
| 2009/0012533 A1 | 1/2009 | Barbagli et al. | |
| 2009/0082722 A1 | 3/2009 | Munger et al. | |
| 2009/0105639 A1 | 4/2009 | Weitzner et al. | |
| 2009/0105645 A1 | 4/2009 | Kidd et al. | |
| 2009/0248043 A1 | 10/2009 | Tierney et al. | |
| 2010/0010475 A1 | 1/2010 | Teirstein et al. | |
| 2010/0256558 A1 | 10/2010 | Olson et al. | |
| 2011/0077590 A1 | 3/2011 | Plicchi et al. | |
| 2012/0182134 A1 | 7/2012 | Doyle | |
| 2012/0184955 A1 | 7/2012 | Pivotto et al. | |
| 2012/0197182 A1 | 8/2012 | Millman et al. | |
| 2012/0220931 A1 | 8/2012 | Cohen et al. | |
| 2013/0138118 A1 | 5/2013 | Doyle | |

FOREIGN PATENT DOCUMENTS

| | | |
|---|---|---|
| WO | 2007008967 A2 | 1/2007 |
| WO | 2009092059 A2 | 7/2009 |

OTHER PUBLICATIONS

State Intellectual Property Office of the People's Republic of China, First Office Action, dated Oct. 30, 2009, Chinese Patent Application 200680025512.7, "Remotely Controlled Catheter Insertion System," with English Translation, (24 pgs. total).

Chinese Application 200680025512.7, State Intellectual Property Office of the People's Republic of China, Office Action dated Feb. 13, 2012.

(56) References Cited

OTHER PUBLICATIONS

Chinese Application 200980102420.8, State Intellectual Propert Office of the People's Republic of China, Office Action dated Feb. 16, 2012.
International Preliminary Report on Patentability, Intl Application PCT/US2009/031357. International Bureau of WIPO, dated Jul. 29, 2010.
International Search Report and Written Opinion, Intl Application PCT/US2009/031357. International Search Authority, U.S. Patent and Trademark Office (ISA/US), dated Mar. 19, 2009.
U.S. Appl. No. 13/051,736, Final Office Action dated Nov. 5, 2012.
Hein et al., "Robot Supported Insertion of Catheters for Hyperthermia and Branch Therapy," Computer Assisted Radiology and Surgery, 1998, pp. 660-663.
Macoviak, "Catheter System for Surgical Access and Circulatory Support of the Heart," USPTO, Official Gazette, vol. 1278, Jan. 6, 2004.
U.S. Appl. No. 13/051,736, Non-Final Office Action dated Jul. 17, 2012.
U.S. Appl. No. 12/903,397, Non-Final Office Action dated Nov. 19, 2012.
Canadian Application 2,646,846, Office Action dated Sep. 19, 2012.
Extended European Search Report dated Apr. 17, 2013; European Application No. 09702983.9.
Japanese Patent Application No. 2010-543298; Office Action dated Mar. 19, 2013.
U.S. Appl. No. 13/461,463, Final Office Action dated Jun. 27, 2014.
U.S. Appl. No. 13/461,463, Non-Final Office Action dated Oct. 31, 2014.
U.S. Appl. No. 12/515,005, Non-Final Office Action dated Apr. 11, 2013.
U.S. Appl. No. 13/078,663, Non-Final Office Action dated Aug. 14, 2014.

* cited by examiner

ADJUSTABLE NOSE CONE FOR A CATHETER POSITIONING SYSTEM

CROSS-REFERENCE TO RELATED APPLICATIONS

The present invention claims the benefit of priority to U.S. Provisional Patent Application No. 61/874,439, entitled "ADJUSTABLE NOSE CONE FOR A CATHETER POSITIONING SYSTEM," filed Sep. 6, 2013, the entire contents of which are incorporated herein by reference.

BACKGROUND

Many procedures involving catheter insertion, such as invasive electrophysiology procedures, rely on fluoroscopy or other radioactive imaging techniques to help navigate and position the catheter within a patient's body at a particular site, such as in the heart or inside a blood vessel in the circulatory system. High dosages of radiation can have long term adverse health effects. A patient may be directly exposed only once or twice to radiation during such procedures and avoid such adverse effects. However, physicians, medical technicians and staff can experience a large cumulative radiation dosage over time, both directly and indirectly, from conducting many procedures.

To protect the operator and staff from this radiation, shielding such as lead aprons, gowns, glasses, skirts, etc., is worn. Such lead clothing, especially a lead apron, is quite heavy and uncomfortable, and its use has been associated with cervical and lumbar spine injury or degradation.

SUMMARY OF THE INVENTION

Various embodiments enable a catheter introducer for use on a catheter positioning system to be rotated around an axis and/or traversed backward and/or forward along the axis. In various embodiments, positioning of an introducer may be enabled by an introducer support configured to be rotated around an axis and/or extended or retracted along the axis. The introducer may be manually operated and/or operated by motors in a nose cone of the catheter positioning system. In other embodiment, positioning of an introducer may be enabled by an adjustable nose cone of the catheter positioning system.

BRIEF DESCRIPTION OF THE DRAWINGS

The accompanying drawings, which are incorporated herein and constitute part of this specification, illustrate exemplary embodiments of the invention, and together with the general description given above and the detailed description given below, serve to explain the features of the invention.

DETAILED DESCRIPTION

Figure 1:
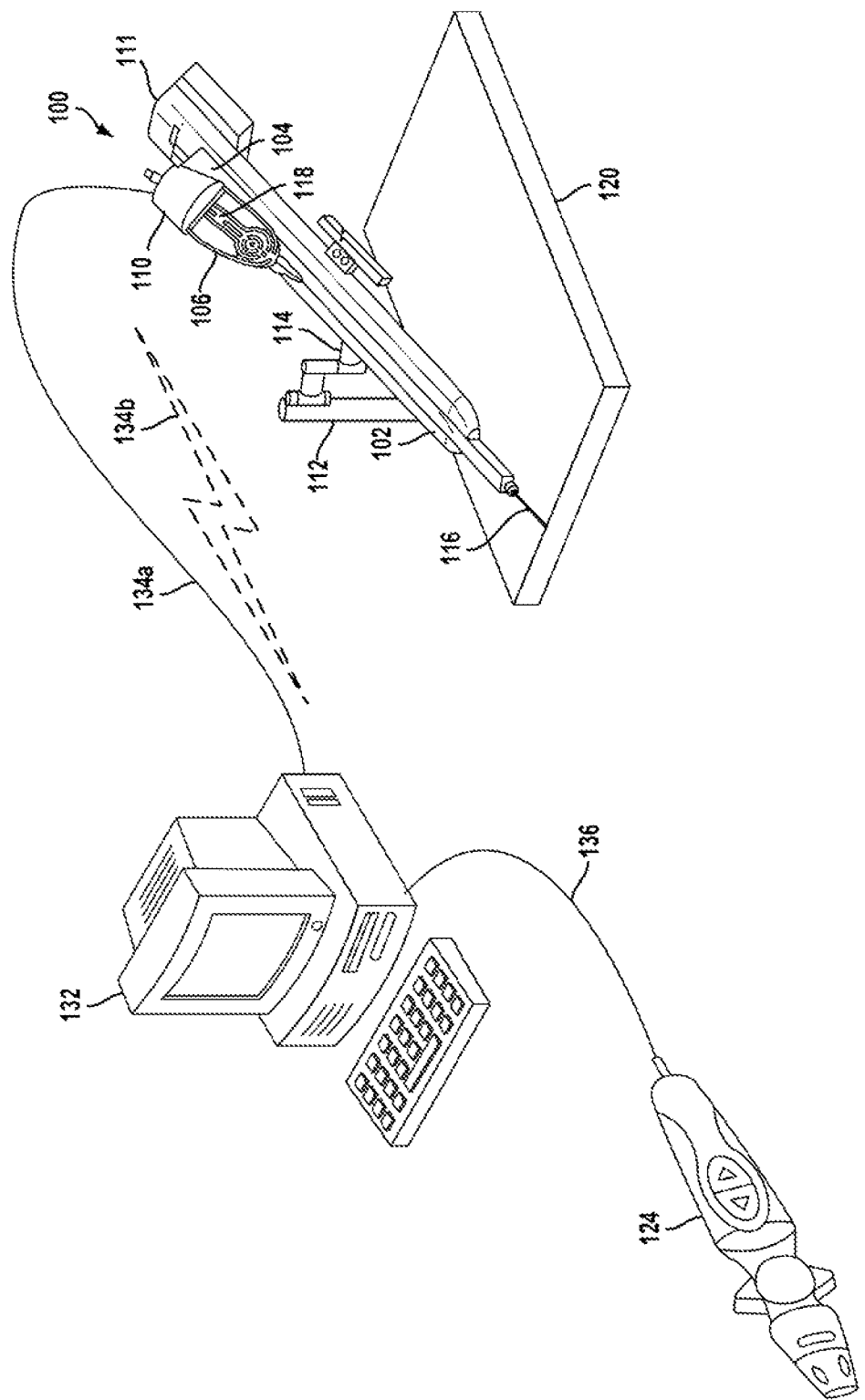
FIG. 1 is a system block diagram illustrating a remote controller, a remotely controlled catheter positioning system, and a programmable control system.

Various embodiments will be described in detail with reference to the accompanying drawings. Wherever possible, the same reference numbers will be used throughout the drawings to refer to the same or like parts. References made to particular examples and implementations are for illustrative purposes and are not intended to limit the scope of the invention or the claims.

The systems, methods, and devices of the various embodiments enable a catheter introducer for use on a catheter positioning system to be rotated around an axis and/or traversed backward and/or forward along the axis. The catheter positioning system enables a physician to remotely control manipulation and insertion of a catheter into a patient while being positioned away from sources of radiation used for imaging or other procedures. The introducer is a component of a catheter positioning system that introduced the catheter into a patient's body, and thus is a structure that contacts both the patient and the catheter positioning system. The catheter positioning system may be used to move the attached catheter through the introducer, and thus within the patient, such as rotating, advancing, or retracting the catheter in relation to the patient or within the patient's body. An example of a catheter positioning system is disclosed in PCT Application PCT/US2009/031357, which published as WO 2009/092059 and is incorporated herein by reference in its entirety.

The introducer is positioned on the catheter positioning system so that a catheter body passes through the introducer to enter a patient's body. The various embodiments enable the introducer to be rotated through various angles and/or to be moved into and out of a patient various distances in order to direct the shaft of the catheter in a particular direction and/or to a particular spot within the patient. Such movement or repositioning of the introducer can resolve problems that may arise during a catheterization procedure, particularly for certain catheters.

During an operation, a physician may wish to manually control the introducer rather than remotely controlling the introducer with the catheter positioning system. Various embodiments may enable the introducer to be easily removed from the catheter positioning system by the physician to enable such manual manipulation. The removable introducer may remain connected with an introducer support when removed from the catheter positioning system, and may enable the introducer to be easily reconnected to the catheter positioning system by the physician.

In various embodiments, positioning of an introducer may be enabled by an introducer support configured to be rotated around an axis and/or extended or retracted along the axis. The introducer support may be manually operated and/or operated by motors in a nose cone of the catheter positioning system. In various embodiments, a portion of the introducer support may be made from flexible materials or otherwise configured to flex. In other embodiment, positioning of an introducer may be enabled by an adjustable nose cone of the catheter positioning system.

FIG. 1 illustrates an embodiment catheter positioning system 100 with a remote controller 124 and a programmable control system 132. The catheter positioning system 100 may further include a sled base 102 coupled with a sled member 104. The sled base 102 may be configured with a drive unit, such as a drive unit 111, to advance or to facilitate advancing the sled member 104 along the sled base 102 towards the body of the patient or back away from the patient. For example, the sled member may be moved with a motor (not shown) in the drive unit 111 at one end of the sled base 102. The sled member 104 may be driven along a rail on the sled base 102 by a drive mechanism (not shown) in the drive unit 111, such as a worm drive, in order to advance or withdraw a catheter (not shown), which may be coupled to the sled member 104 or to a component that is coupled to the sled member 104.

The sled base 102 may be held in position above a patient and/or an operating table 120 by a bridge (not shown) or support arm 112. The support arm 112 may be coupled to a sled base support structure 114 through articulating joints. When moved into a working position, the sled base support structure 114 hold the sled base 102 in a fixed position and orientation. The arm 112 and the sled base support structure 114 may further be extended or rotated to position the sled base 102 relative to a patient on the operating table 120. The sled base 102 may also include a nose cone coupled to an introducer 116 that supports insertion of the catheter into a patient. The sled base 102 and/or nose cone may include one or more motors which may drive one or more actuators, such as gears, to change a position/orientation of the introducer 116, thereby allowing an operator to control the position/orientation of the introducer 116 via the remote controller 124. A catheter may be advanced along the sled base 102 by the sled member 104 so that the body of the catheter passes through the nose cone and introducer 116 and into the patient.

The sled base 102 may include a sterile barrier (not shown) configured to support and protect the catheter. The sterile barrier may include a resealable delivery channel configured to receive and guide the catheter along the sled base as it is advanced by the sled member 104. For example, the body of the catheter may be inserted into the delivery channel and then the catheter handle 118 may be connected to the sled member 104 (such as by using the modular plate 106 discussed below) such that the catheter body is driven forward by translation of the sled member 104 along the resealable delivery channel in the sled base 102 and through the nose cone and introducer 116 into the patient.

The sled member 104 may be equipped with a modular plate 106 to which a catheter handle 118 may be attached. The modular plate 106 may be configured to be removable such that many alternative modular plates 106, may be swapped in and out. Thus, the catheter positioning system may be used with many different types of catheters by the use of a corresponding modular plate 106, such as alternative plates that are adapted for use with alternative catheters or catheter handles. Depending on the kind of catheter that is desired for a given procedure, an appropriate modular plate 106 may be attached to the sled member 104 and the catheter and/or the catheter handle 118 may be attached to the module plate 106. The modular plate 106 may integrate with any actuators on the catheter handle 118, thereby allowing an operator to control the actuators via the remote controller 124.

The sled member 104 may be rotated by a drive mechanism 110 in order to rotate a catheter connected to the modular plate 106. The rotation of the sled member 104, such as by actuating the drive mechanism 110, may be controlled remotely via the remote controller 124. By controlling translation along the sled base 102, the rotation of the sled member 104, and the actuation of the catheter's handle via the modular plate 106, an operator may position or use the catheter in any way necessary for a desired operation. Further, an operator may control each of these degrees of freedom (i.e., translation, rotation, and actuation) remotely with the remote controller 124.

A remote controller 124 may be connected to a system processor of the programmable control system 132 by one or more of a wired connector 136 or a wireless data link (not shown), such as a Bluetooth link. The system processor of the programmable control system 132 may also be connected to the catheter positioning system 100 and the various motors within the catheter positioning system 100, such as nose cone motors, sled motors, sled base motors, etc., by one or more wired connector 134a or a wireless data link 134b. The system processor of the programmable control system 132 may output control signals to actuate the motors of the catheter positioning system 100 based on inputs from the remote controller 124 and/or based on a calibration sequence, a training sequence or a programming sequence, such as programmed movements for automatic positioning of the catheter. Programmed movements of the catheter positioning system 100 may be input prior to a medical procedure, such as by entering commands into the system processor of the programmable control system 132 (e.g., via a keyboard) or by calibrating and/or training the system, such as through manipulation of the remote controller 124, selection of other real-time operations from the programmable control system 132, and so on. In particular, the programmable control system 132 may be configured with processor-executable instructions to issue drive or power commands to each of the motors in the catheter positioning system 100 to control the relative rotations of each motor to rotate the introducer 116 about an axis and/or traverse the introducer 116 backward or forward along the axis.

The system processor of a programmable control system 132 may be implemented or performed with a general purpose processor, a digital signal processor (DSP), an application specific integrated circuit (ASIC), a field programmable gate array (FPGA) or other programmable logic device, discrete gate or transistor logic, discrete hardware components, or any combination thereof designed to perform the functions described herein. A general-purpose processor may be a microprocessor, but, in the alternative, the processor may be any conventional processor, controller, microcontroller, or state machine. A processor may also be implemented as a combination of computing devices, e.g., a combination of a DSP and a microprocessor, a plurality of microprocessors, one or more microprocessors in conjunction with a DSP core, or any other such configuration. Alternatively, some operations may be performed by circuitry that is specific to a given function.

Figure 2:
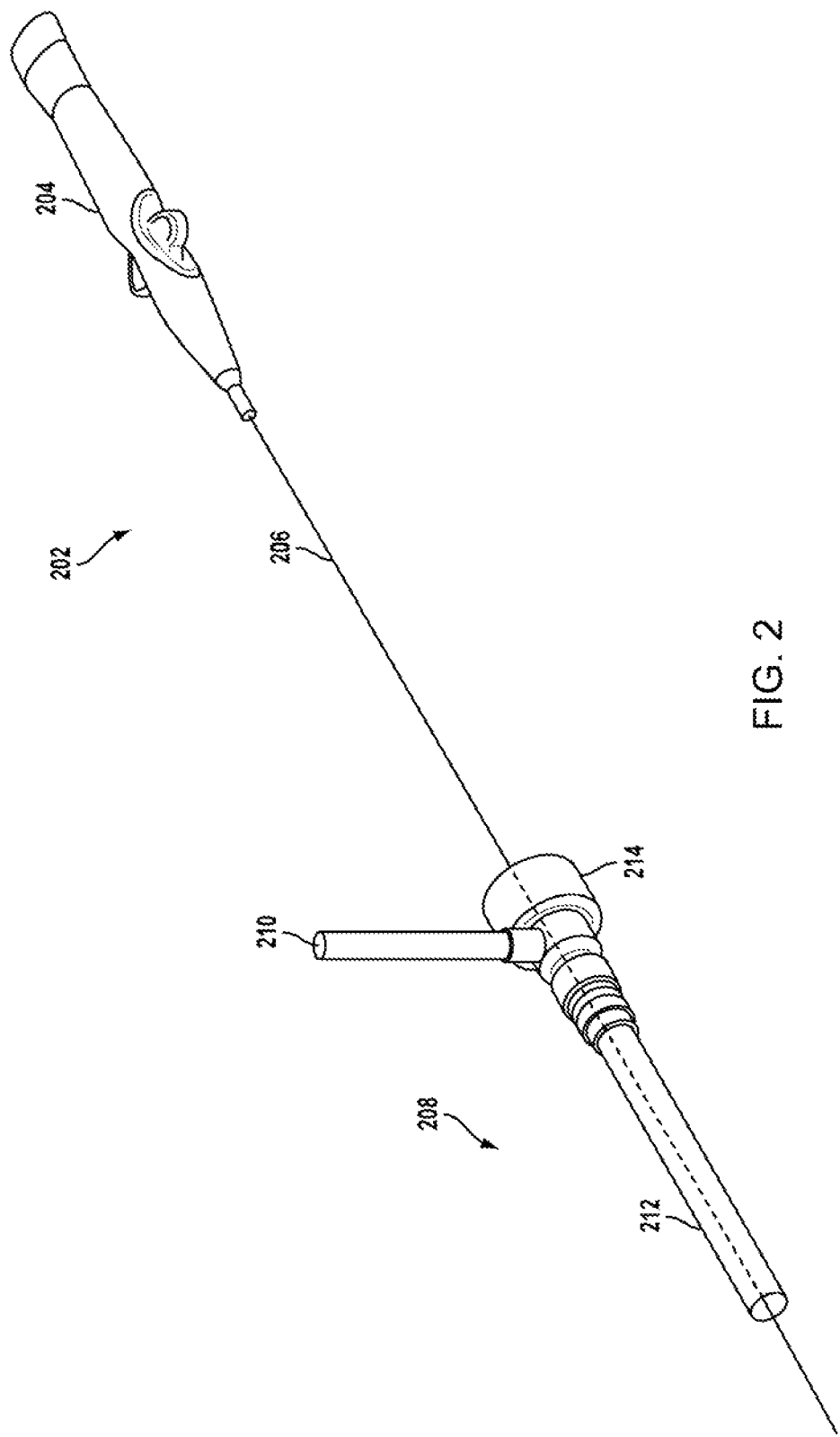
FIG. 2 is a diagram illustrating an oblique view of a catheter body threaded through an introducer.

FIG. 2 illustrates a catheter 202 assembly having portions that pass through an introducer 208. The body 206 of the catheter 202 may extend from the handle 204 of the catheter 202 toward the introducer 208. The introducer 208 may include a throat 214 connected to a sheath 212. The throat 214 and sheath 212 may form a hollow passage through which the body 206 of the catheter 202 may pass. The introducer 208 may also include one or more irrigation port 210 configured to enable fluids to be passed through the irrigation port 210 into and/or out of the throat 212 and/or sheath 212. The introducer 208 may guide the body 206 of the catheter 202 into/out of a patient's body, such as at a catheter insertion site. The introducer 208 may further provide mechanical support and protection against buckling or bending of the body 206 of the catheter 202 as the body 206 of the catheter 202 is advanced, retracted, and/or held stationary through the introducer 208.

While illustrated as a straight tube with a straight tip, the sheath 212 of the introducer 208 may have other shapes, such as a curved, angled, preformed tip, etc. Additionally, the length of the sheath 212 of the introducer 208 illustrated in FIG. 2 is not to scale and is provided merely as an illustration. The sheath 212 of the introducer 208 may have different lengths. The introducer 208 may be rotated at various angles and/or may be moved into and out of a patient various distances to direct the shaft 206 of the catheter 202 in a particular direction and/or to a particular spot within the patient. As an example, an introducer 208 with an angled tip may be moved forward and rotated to position a tip of the shaft 206 of the catheter 202 behind an organ in a patient's body. As discussed above, the introducer 208 may be held in a nose cone of the catheter positioning system 100. In an embodiment, the introducer 208 may be held in a nose cone by an introducer clamp which may fasten over a portion of the throat 214 of the introducer 208. In another embodiment, the introducer 208 may include threads within the throat 214 and may screw onto a threaded portion of a nose cone.

Figure 3:
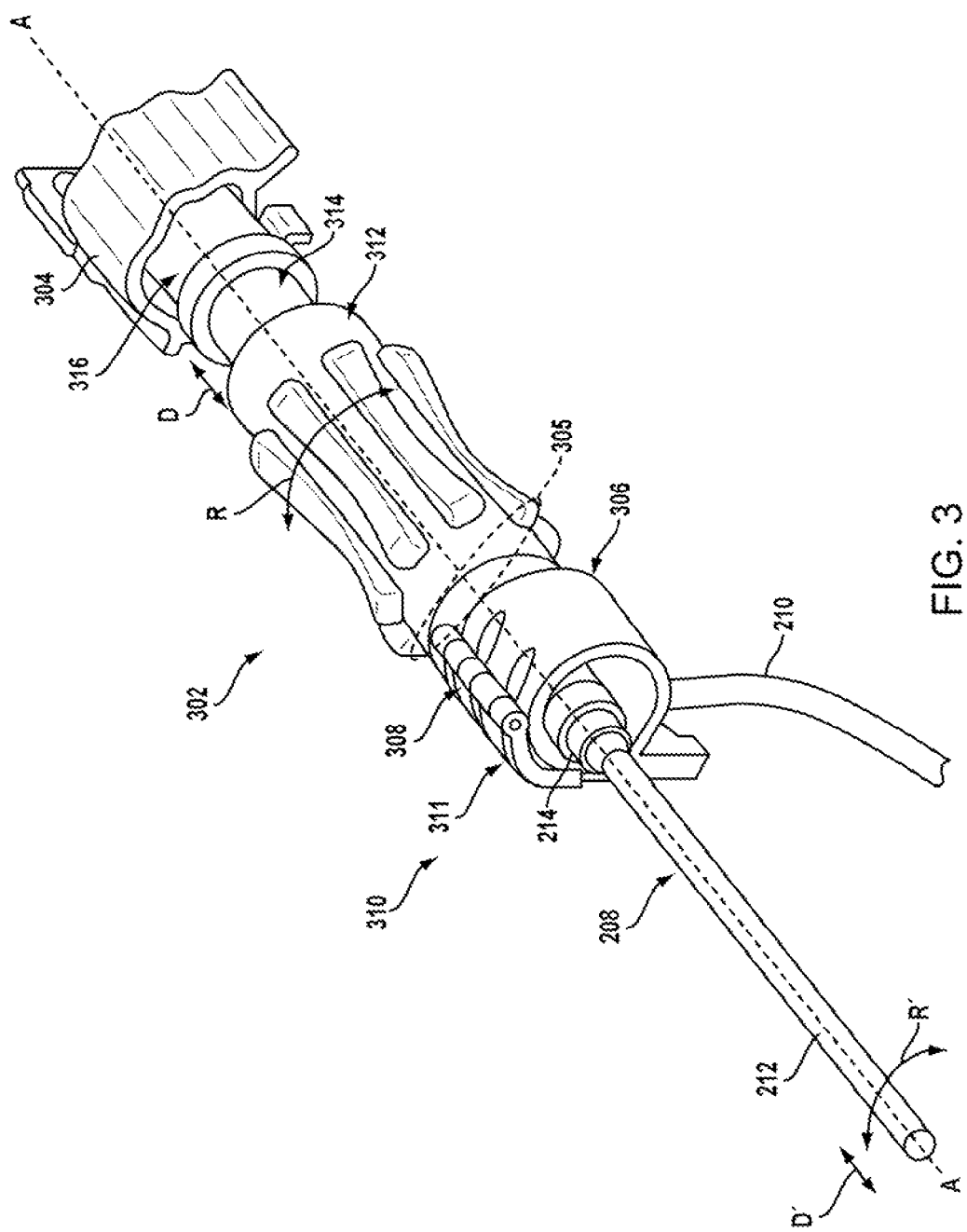
FIG. 3 is a diagram illustrating an oblique view of an embodiment adjustable introducer support.

FIG. 3 illustrates an introducer support 302 which may be connected between a nose cone and an introducer 208 to enable the introducer 208 to be rotated through an angle R' around an axis A and/or to be extended or retracted a distance D' along the axis A. The introducer support 302 may also include a flexible section or flex structure configured to flex to enable the introducer 208 to move in response to a force exerted on the introducer 208 while connected to the introducer support 302. Such flexure may reduce pressures applied to the patient at the point of entry of the introducer due to movement of the patient and/or the catheter positioning system. The introducer support 302 may include a hollow outer cylindrical body 312 encircling a hollow central shaft 314.

The outer cylindrical body 312 may be configured to slide over the central shaft 314 to rotate through an angle R around the central shaft 314 and axis A and to extend or retract a distance D along the central shaft 314 and axis A. In some embodiments, the outer cylindrical body 312 may rotate about the central shaft 314. For example, in some embodiments, the outer cylindrical body 312 may rotate 360 degrees clockwise or counterclockwise around the central shaft 314 and axis A. In an embodiment, an end of the outer cylindrical body 312 may traverse a distance of between about 1 inch and about two inches and preferably about 1.5 inches in one direction along the axis A to move from a fully retracted to a fully extended position and may traverse a distance of between about 1 inch and about two inches and preferably about 1.5 inches in the opposite direction along the axis A to move from the fully extended position to the fully retracted position.

The introducer support 302 may be attached to a clamp 304 of a nose cone of a catheter positioning system by a friction or a snap fit. The clamp 304 may fasten over an attachment end 316 of the central shaft 314 of the introducer support 302 to securely hold the central shaft 314 of the introducer support 302 in place.

An end of the outer cylindrical body 312 opposite the attachment end 316 may include an introducer clamp 310 formed from a fixed clamp portion 311 extending from the outer cylindrical body 312 and a clamp tab 306 rotationally coupled to the fixed clamp portion 311 by a hinge 308. The clamp tab 306 may fasten to the fixed clamp portion 311 by friction or a snap fit and the resulting introducer clamp formed from the fixed clamp portion 311 and clamp tab 306 may fasten over a throat 214 of an introducer 208 to securely hold the introducer 208 in place. In some embodiments, the clamp tab 306 may include teeth or other adjustable gripping and/or tensioning mechanisms that allow the clamp tab 306 to clamp to different sizes or configurations of the throat 214.

In an embodiment, the fixed clamp portion 311 and/or the clamp tab 306 may include cutouts configured to enable the irrigation port 210 of the introducer to pass through the introducer clamp formed from the fixed clamp portion 311 and clamp tab 306.

A catheter body may pass through the clamp 304 the introducer support 302 and the introducer 208 when the clamp 304, the introducer support 302, and the introducer 208 are coupled together. The clamp 304 of the nose cone may be opened and the introducer support 302 and introducer 208 may be removed from the nose cone as a single unit, thereby enabling a doctor or operator to manipulate the introducer support 302 and introducer 208 independent of a catheter positioning system.

In an embodiment, the clamp 304, introducer support 302, and introducer 208 may be coupled together and the outer cylindrical body 312 may be slid over the central shaft 314 and may directly or indirectly engage the introducer 208 and the shaft 212, such as through the introducer clamp 310. As the outer cylindrical body 312 is rotated through an angle R around the central shaft 314 and axis A, a corresponding rotation may be imparted to the shaft 212 of the introducer 208 to rotate the shaft 212 a distance R' around the axis A.

In an embodiment, the clamp 304, introducer support 302, and introducer 208 may be coupled together and the outer cylindrical body 312 may be slid over the central shaft 314 and may directly or indirectly engage the introducer 208 and the shaft 212, such as through the introducer clamp 310. As the outer cylindrical body 312 is extended or retracted a distance D along the central shaft 314 and axis A, a corresponding extension or retraction may be imparted to the shaft 212 of the introducer 208 to extend or retract the shaft 212 a distance D' along the axis A. In this manner, the introducer support 302 may be rotated to various angles and/or may be moved into and out of a patient various distances to direct the shaft 212 of the introducer 208 and/or a shaft of a catheter passed through the introducer support 302 and introducer 208 in a particular direction and/or to a particular spot within the patient.

In an embodiment, the outer cylindrical body 312 may include a flexible portion 305 enabling the introducer clamp 310 (e.g., formed from the fixed clamp portion 311 and clamp tab 306 and the introducer 208) to flex in response to a force exerted on the introducer 208, such as force resulting from the movement of a patient while the sheath 212 of the introducer 208 is inserted in the patient. The flexible portion 305 may be formed in any manner enabling the introducer clamp 310 (e.g., formed from the fixed clamp portion 311 and clamp tab 306 and the introducer 208) to flex in one or more of the rotational direction or the linear direction, such as relative to the outer cylindrical body 312. In other words, the flexible portion 305 may be configured with one or more flexibility parameters, such as torsional flexibility, compressive flexibility, and tensile flexibility. As an example, the flexible portion 305 may comprise one or more bellows formed in the outer cylindrical body 312. As another example, the flexible portion 305 may be formed from an elastic material that is flexible or at least less rigid than other portions of the outer cylindrical body 312. The length of the flexible portion 305 along the outer cylindrical body 312 and the axis A may depend upon the desired amount of flexibility (i.e., the total deflection or displacement from a normal dimension) of the flexible portion 305. For example, longer lengths of the flexible portion 305 may be more flexible and enable more flexile deflection compared to a shorter flexible portion 305. The ability of the introducer support 302 to flex may reduce or minimize disruption in patient comfort at the introducer site when a patient moves while the sheath 212 of the introducer 208 is inserted into the patient's body. Additionally, the ability of the introducer support 302 to flex may facilitate attaching the introducer 208 into the introducer clamp 310 (e.g., formed from the fixed clamp portion 311 and clamp tab 306) because precise alignment between the introducer 208 and the clamp may not be necessary to fit the introducer 208 in the clamp.

Figure 4:
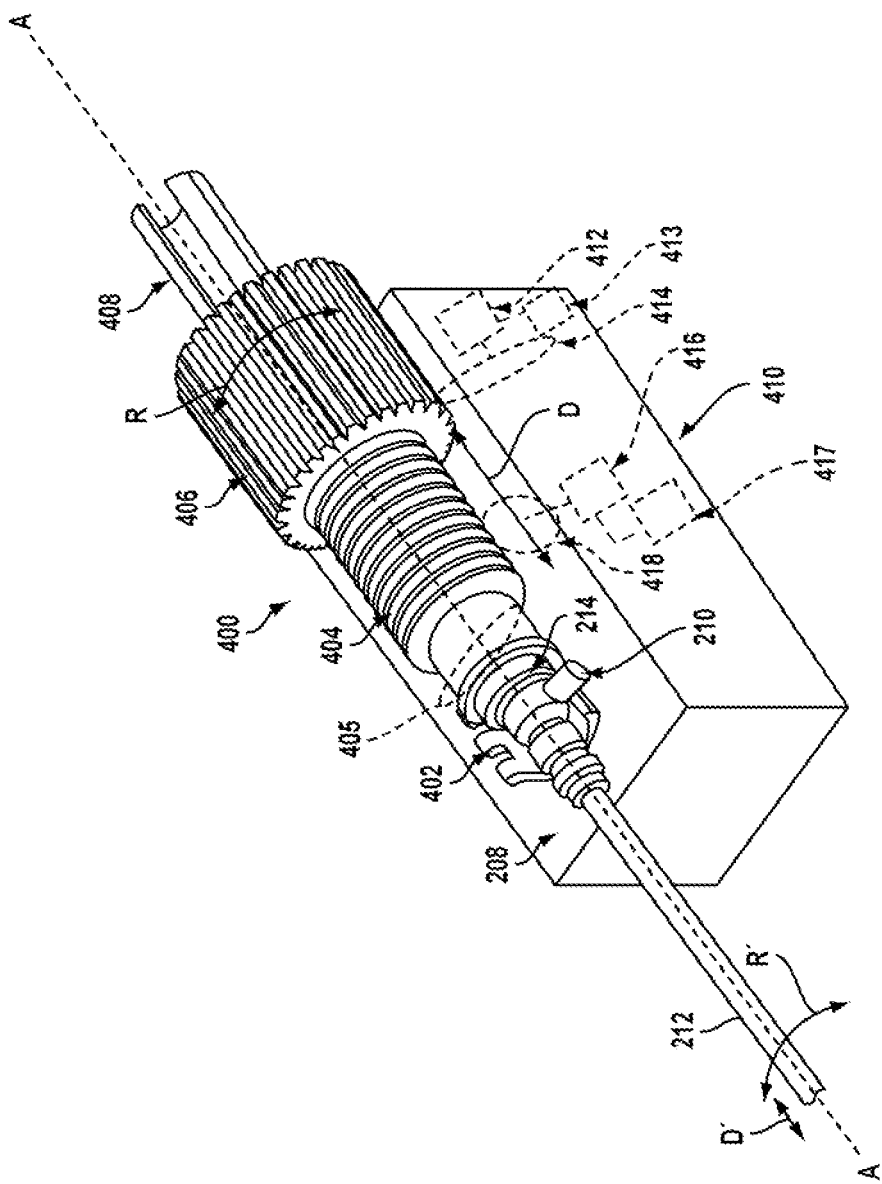
FIG. 4 is a component diagram illustrating an embodiment adjustable introducer support and nose cone portion.

FIG. 4 illustrates an introducer support 400 and portion of a nose cone 410 of a catheter positioning system to which the introducer support 408 may be connected. The portion of the nose cone 410 is shown as a rectangular block for ease of illustration. The portion of the nose cone 410 and the nose cone 410 may take many shapes, examples of which are shown and described in greater detail in connection with other figures. The introducer support 400 may be coupled to the nose cone 410 and the introducer 208. The introducer 400 may be configured to enable the introducer 208 to be rotated through an angle R' around an axis A and/or to be extended or retracted a distance D' along the axis A.

The introducer support 400 may include a hollow rotating portion 406 that encircles a hollow extending portion 404. The hollow rotation portion 406 may be configured to encircle the hollow extending portion in an inner circumferential cavity as the hollow extending portion 404 extends or retracts along the axis A. The outer circumference of the hollow rotating portion 406 may include gear teeth formed from grooves and ridges running parallel to the axis A. The gear teeth may allow the hollow rotating portion 406 to be rotated about the axis A by a drive that engages the gear teeth. The outer circumference of the hollow extending portion 404 may include a series of circumferential engaging members, such as a series of circumferential gear teeth formed from a series of circular grooves and ridges running around the outer circumference of and along the length of the hollow extending portion 404. Each ridge and groove may be oriented in a respective plane perpendicular to the axis A. The hollow extending portion 404 may be configured to slide into and/or out of the hollow rotating portion 406 a distance D along the axis A.

The hollow rotating portion 406 may be configured to contact or otherwise grip the hollow extending portion 404 such that when the hollow rotating portion 406 is rotated in either direction around the axis A, an corresponding rotation in the same direction of rotation is imparted to the hollow extending portion 404.

In an embodiment, the hollow rotating portion 406 may rotate 360 degrees in either direction around the axis A.

In an embodiment, the hollow extending portion 404 may traverse a distance of between about 1 inch and about two inches and preferably about 1.5 inches in a first direction along the axis A to move from a fully retracted to a fully extended position. The hollow extending portion 404 may traverse a distance between about 1 inch and about two inches and preferably about 1.5 inches in an opposite direction of the first direction along the axis A to move from the fully extended position to the fully retracted position.

The introducer support 400 may include a support extension 408 rotationally coupled to the hollow rotating portion 406 and configured to be secured in a clamp of the nose cone 410 of the catheter positioning system by friction or a snap fit. As an example, a clamp may fasten over the support extension 408 of the introducer support 400 to secure the introducer support 400 in place.

An end of the hollow extending portion 404 opposite the support extension 408 may include an introducer clamp formed from a fixed clamp portion 402 extending from the hollow extending portion 404 and a clamp tab (not shown) rotationally coupled to the fixed clamp portion 402 by a hinge (not shown). The clamp tab may fasten to the fixed clamp portion 402 by friction or a snap fit and the resulting introducer clamp formed from the fixed clamp portion 402 and clamp tab may fasten over a throat 214 of an introducer 208 to securely hold the introducer 208 in place.

In an embodiment, the fixed clamp portion 402 and/or the clamp tab may include cutouts configured to enable the irrigation port 210 of the introducer to pass through the introducer clamp formed from the fixed clamp portion 402 and clamp tab.

A catheter body may pass through the clamp, the introducer support 400 and the introducer 208, such as when the clamp, introducer support 400, and introducer 208 are coupled together. The clamp of the nose cone 410 securing the support extension 408 may be opened and the introducer support 400 and introducer 208 may be removed from the nose cone 410 as a single unit, thereby enabling a doctor or operator to manipulate the introducer support 400 and introducer 208 independent of a catheter positioning system.

In an embodiment, in order to drive the hollow rotating portion 406, the portion of the nose cone 410 may include a first motor 412 coupled to a first gear 414. The teeth of the first gear 412 may be configured to interface with the gear teeth of the hollow rotating portion 406 when the introducer support 400 is secured in the nose cone 410. The first gear 414 may interface with the gear teeth of the hollow rotating portion 406 such that the motor 412 may turn the first gear 414, which causes the hollow rotating portion 406 to rotate. As discussed above, the hollow rotating portion 406 may be coupled to the hollow extending portion 406 such that rotation of the hollow rotating portion 406 causes the hollow extending portion 404 and the introducer 208 secured in the clamp of the hollow extending portion 404 to rotate. In this manner, the rotation of the first gear 414 by the first motor 412 may rotate the hollow rotating portion 406 through an angle R around the axis A. A corresponding rotation may be imparted to the shaft 212 of the introducer 208 to rotate the shaft 212 through an angle R' around the axis A.

In some embodiments, a sensor 413 may be coupled to the first motor 412, such as to the motor driver circuit, to a data interface, to a rotational shaft, or to a power line for the first motor 412. The sensor 413 may be configured to detect an irregularity in the rotational movement of the first motor 412, such as a rotational irregularity, a drive current irregularity, or other drive irregularity in the motor 412 that indicates that a potential physical obstruction to the rotational movement has been encountered, or that an error condition exists. The detection of an obstruction condition may be treated as a signal to stop the movement of the motor 412 to avoid or prevent an undesirable condition.

While the sensor 413 is described in connection with the motor 412, other positions and couplings of the sensor 413 are possible. For example, in other embodiments, sensors may be located at an interface between the nosecone, or components of the nosecone, and the catheter positioning system. Sensors may be located so that they are in electrical series with any nosecone drive mechanism. Alternatively or additionally, sensors may be located in the nosecone with a feedback mechanism to the catheter positioning system. For example, the sensors may be simple low cost mechanisms, such as a limit switch. In such an embodiment, activation of the sensors may signal the catheter positioning system that a specific deflection, rotation, pressure or other limit quantity has been reached. In more complex embodiments, the sensors may be force sensors that signal when a specific force has been reached. The complexity and cost of the sensors may determine where the sensors are located. For example, expensive and/or complex sensors may be positioned away from the nosecone, such as at or near the catheter positioning system, or catheter positioning system interface. Cheaper, simpler sensors may be located on or within the nosecone itself and may be disposable.

In an embodiment, in order to drive the hollow extending portion 404, the portion of the nose cone 410 may include a second motor 416 coupled to a second gear 418. The teeth of the second gear 418 may be configured to interface with the gear teeth (e.g., circumferential ridges and grooves) of the hollow extending portion 404 when the introducer support 400 is secured in the nose cone 410. The second gear 418 may interface with the gear teeth of the hollow extending portion 404 such that the motor 416 may turn the second gear 418, which causes the hollow extending portion to move along the axis A. In some embodiments, the second gear 418 may act as a rack gear extending and/or retracting the hollow extending portion 404, and the introducer 208 secured in the clamp of the hollow extending portion 404, a distance D along the axis A toward and/or away from the hollow rotating portion 406. In this manner, the rotation of the second gear 418 by the second motor 416 may extend or retract the hollow extending portion 404 a distance D along the axis A, causing a corresponding extension or retraction to be imparted to the shaft 212 of the introducer 208 to extend or retract the shaft 212 a distance D' along the axis A.

In some embodiments, a sensor 417 may be coupled to the second motor 416, such as to the motor driver circuit, to a data interface, to a rotational shaft, or to a power line for the second motor 416. The sensor 417 may be configured to detect an irregularity in the rotational movement of the second motor 417, such as a rotational irregularity, a drive current irregularity, or other drive irregularity in the second motor 417 that indicates that a potential physical obstruction to the linear extension or retraction movement of the hollow extending portion 404 has been encountered, or that an error condition exists. The detection of an obstruction condition by the sensor 417 may be treated as a signal to stop the movement of the motor 416 to avoid or prevent an undesirable condition. While the sensor 417 is described in connection with the motor 416, other sensor positions and couplings are possible.

The activation of the first motor 412 and/or second motor 416 and the resulting rotation of the first gear 414 and/or second gear 418, respectively, may enable the introducer support 400 to be rotated at various angles and/or to be moved into and out of a patient various distances to direct the shaft 212 of the introducer 208 and/or a shaft of a catheter passed through the introducer support 400 and introducer 208 in a particular direction and/or to a particular spot within the patient remotely without directly manually interacting with the introducer support 400.

In an embodiment, the hollow extending portion 404 may include a flexible portion 405 enabling the introducer clamp formed from the fixed clamp portion 402 and clamp tab and the introducer 208 to flex in response to a force exerted on the introducer 208, such as force resulting from the movement of a patient while the sheath 212 of the introducer 208 is inserted in the patient. The flexible portion 405 may be formed in any manner enabling the clamp formed from the fixed clamp portion 402 and clamp tab and the introducer 208 to flex. As an example, the flexible portion 405 may comprise one or more bellows formed in the hollow extending portion 404. As another example, the flexible portion 405 may be formed from a flexible material or an elastic material that is less rigid than other portions of the hollow extending portion 404. As discussed above, the length of the flexible portion 405 may depend upon the amount of flexibility or total the deflection that is desired to prevent or reduce trauma to the patient and/or facilitate attaching the introducer 208 into the clamp formed from the fixed clamp portion 402 and clamp tab.

Figure 5A:
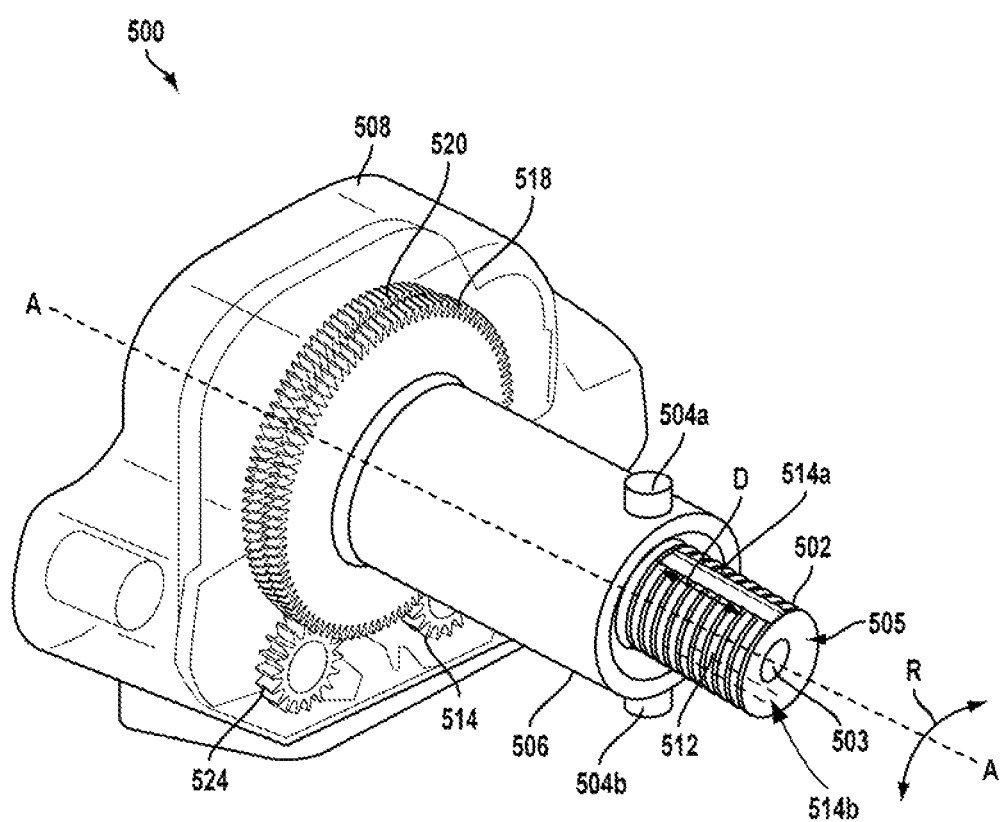
FIG. 5A is a diagram illustrating a cut away view of an embodiment adjustable nose cone.
Figure 5B:
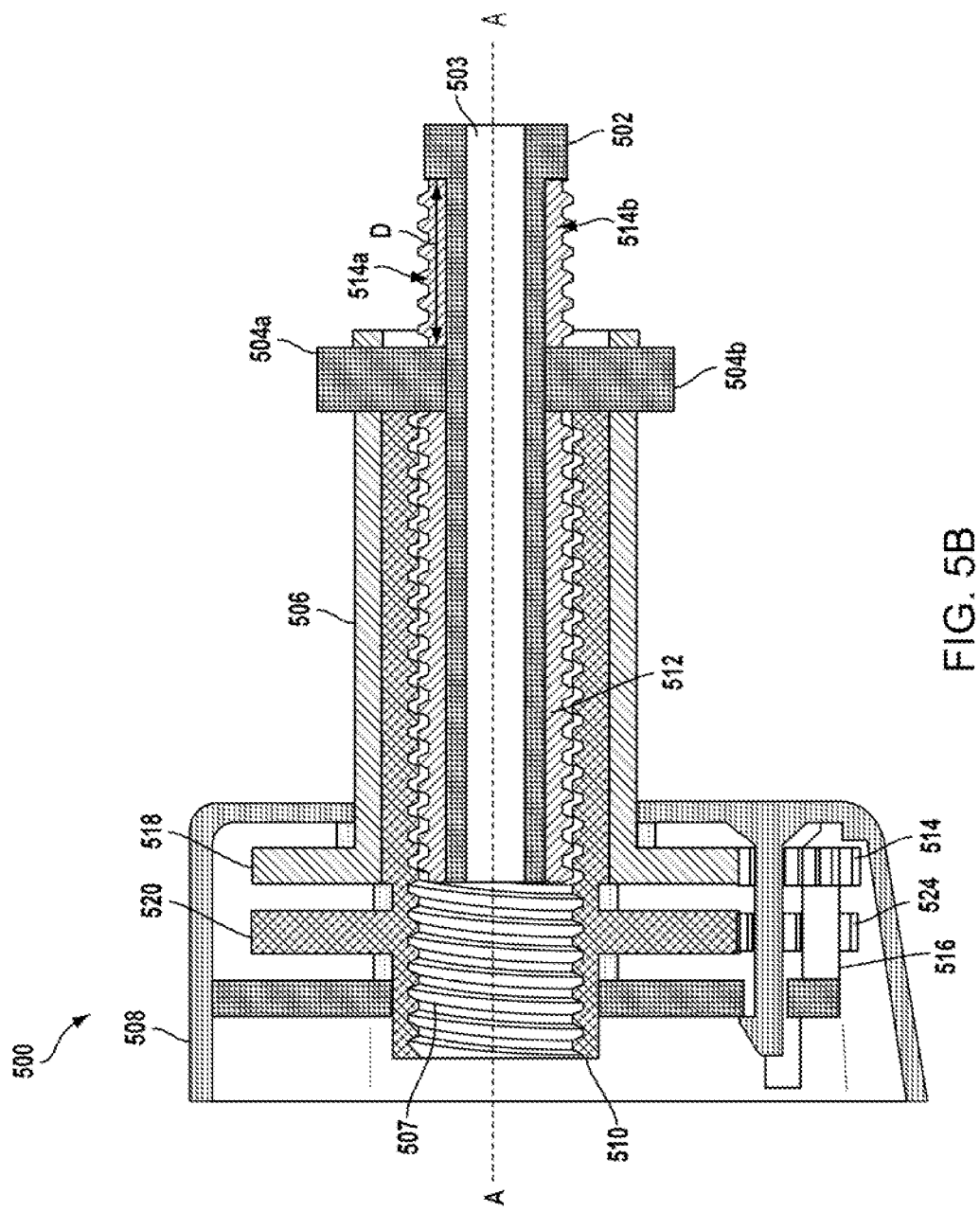
FIG. 5B is a diagram illustrating a cross sectional view of the embodiment adjustable nose cone shown in FIG. 5A.
Figure 5C:
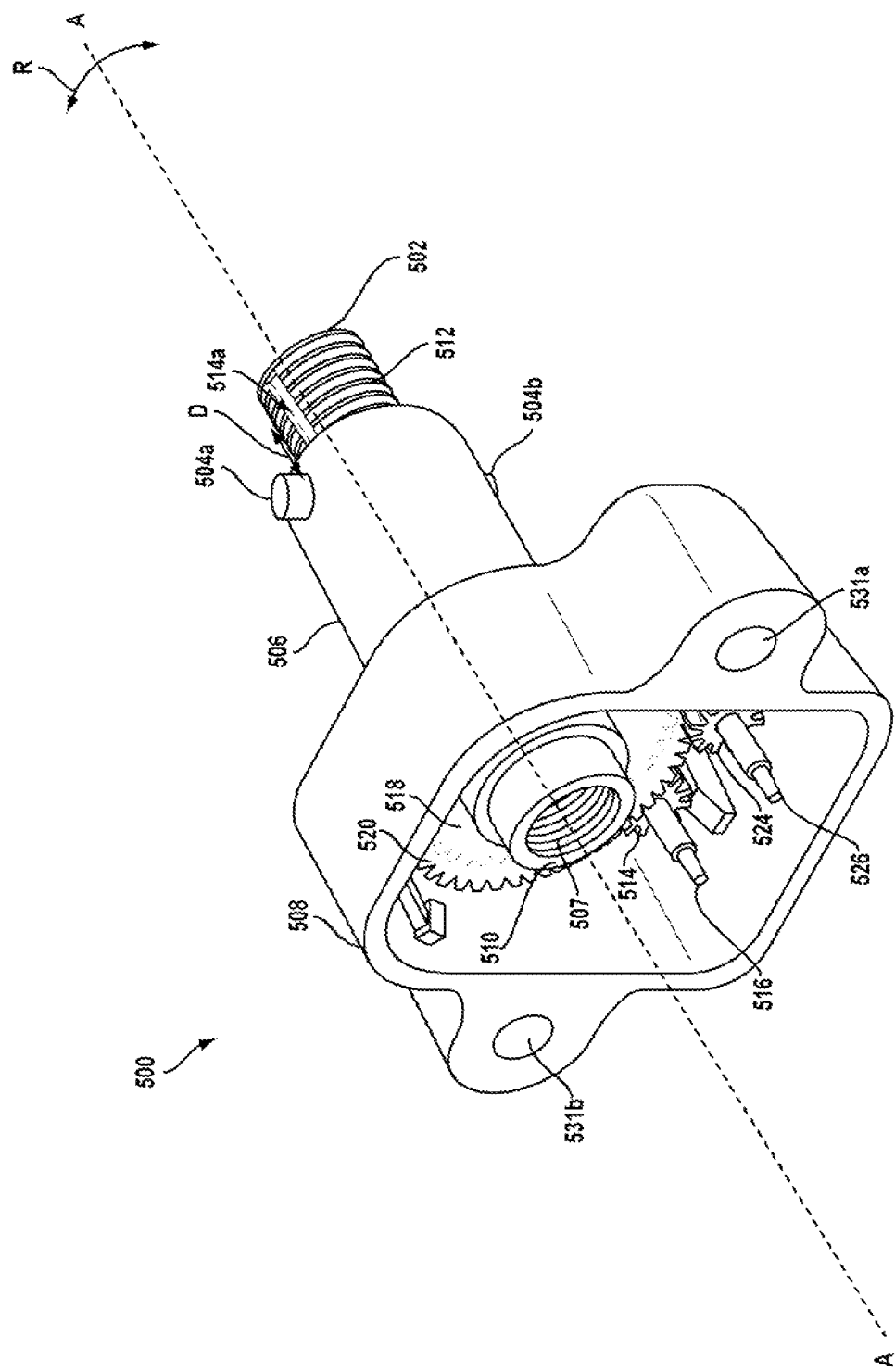
FIG. 5C is a diagram illustrating an oblique view of the rear of the embodiment adjustable nose cone of FIG. 5A.

FIG. 5A, FIG. 5B, and FIG. 5C illustrate various views of an embodiment adjustable nose cone 500. FIG. 5A illustrates a cut away view of a nose cone 500 showing the various components of an embodiment of the nose cone 500 and including the relationship of the components of the nose cone 500, which are positioned outside the housing 508, to the components that are positioned inside the housing 508. Although example relationships are shown, they are illustrative in nature and are not intended to be limiting. Other configurations are possible.

The nose cone 500 may include the housing 508, a sheath holder 502, and an outer cylinder 506. The nose cone 500 may further include a concentric an inner cylinder 510, which is shown in the cross sectional view of FIG. 5B. The sheath holder 502 may be supported within the hollow center of the inner cylinder 510. The inner cylinder 510 and sheath holder 502 may be supported within the hollow center of the outer cylinder 506.

The inner cylinder 510 may rotate within the outer cylinder 506. The inner cylinder 510 and the outer cylinder 506 may both be held in a fixed position along the axis A by the housing 508 while still being enabled to rotate around the axis A.

The sheath holder 502 may be hollow with a central passage 503 that a catheter body may pass through. The outer circumference of the sheath holder 502 may include threads 512. An end 505 of the sheath holder 502 may be configured to support an introducer for a catheter, such as introducer 208 discussed above. As examples, an introducer, such as the introducer 208, may screw onto the end 505 of the sheath holder 502 or may clamp onto the end 505 of the sheath holder 502. Pins 504a and 504b may pass through the outer cylinder 506 and may extend into grooves 514a and 514b (visible in FIG. 5B) in the surface of the sheath holder 502.

An end of the outer cylinder 506 may be configured with a toothed gear 518 positioned within the housing 508. An end of the inner cylinder 508 may be configured with a toothed gear 520 positioned within the housing 508. The toothed gear 518 may interface with a drive gear 514 and the toothed gear 520 may interface with a drive gear 524.

FIG. 5B presents a cross sectional view of the nose cone 500 including threads 507 that may extend along an inner circumference of the inner cylinder 510. The threads 507 may interface with the threads 512 of the sheath holder 502 and may rotationally engage the threads 512 to move the sheath holder 502 back and forth along the A axis. FIG. 5B further illustrates the respective engagement between the drive gears 514, 524 and the toothed gears 518, 520.

FIG. 5C illustrates a rear view of the nose cone 500. The nose cone 500 may include attachment points 531a and 531b that may be used for coupling the nose cone 500 to a catheter positioning system, such as via snaps and/or friction, screw connectors, or other connection mechanism. The nose cone 500 may be coupled to a catheter positioning system at several points. For example, a first shaft 526 and a second shaft 516 may extend from and may be configured respectively to drive the gear 524 and the gear 514.

The first shaft 524 may interface with a motor of the catheter positioning system, such as a motor in a sled base. Further, the second shaft 516 extending from and configured to drive gear 514 may interface with another motor in the catheter positioning system, for example another motor in the sled base. In other embodiments, the respective motors that drive the first and second shafts 526, 516 may be positioned in the nose cone 500. The second shaft 516 extending from gear 514 may be rotated by a drive motor that may drive the rotation of the gear 514.

Rotation of the gear 514 may cause the toothed gear 518 of the outer cylinder 506 to rotate the outer cylinder 506 around the axis A. The rotation of the outer cylinder 506 around the axis A may cause the pins 504a and 504b to rotate and to exert force against the sides of the grooves 514a and 514b of the sheath holder 502 to rotate the sheath holder 502 in a direction through an angle R about the axis A. The gear 514 may drive the toothed gear 518 and the outer cylinder 506 to rotate in either direction.

The shaft first 526 extending from and coupled to the gear 524 may be rotated by a drive motor causing rotation of the gear 524. Rotation of the gear 524 may cause the toothed gear 520 of the inner cylinder 510 to rotate the inner cylinder 510 around the axis A. The rotation of the inner cylinder 510 around the axis A may cause the threads 507 on the inner circumference of the inner cylinder 510 to interact with the threads 512 of the sheath holder 502 to drive the sheath holder 502 forward or backward a distance D along the axis A. Counter rotation of the inner cylinder 510 may be prevented by the pins 504a and 504b interacting with the sides of the grooves 514a and 514b.

In an embodiment, the anti-rotation feature of the pins 504a and 504b in the grooves 514a and 514b in combination with rotation (or position locking/holding) of the inner cylinder 510 and/or the outer cylinder 506 may be used to control the rotation and extension of the sheath holder 502 and an introducer coupled to an end 505 of the sheath holder 502 (see FIG. 5A). As an example, the end 505 of the sheath holder 502 and an introducer coupled to the end 505 may be extended by causing the inner cylinder 510 to rotate. The rotation of the inner cylinder 510 and its threads 507 may impart a linear driving force on the threads 512 of the sheath holder 502. While the inner cylinder 510 is being rotated, such as to extend or retract the sheath holder 502, the outer cylinder 506 including the pins 504a and 504b may be held stationary (for example by holding the shaft 516 and gear 514 stationary). In this manner, the pins 504a and 504b may interact with the sides of the grooves 514a and 514b may prevent the rotation of the sheath holder 502. By preventing the rotation of the sheath holder 502, the rotational force imparted from the rotating threads 507 of the inner cylinder 510 on the threads 512 may be translated into a lateral force along the axis A to drive the sheath holder 502 out of the inner cylinder 510 or into the inner cylinder 510. The pins 504a and 504b may be held stationary relative to the axis A as the sheath holder 502 extends and retracts and may in turn prevent the sheath holder 502 from rotating or counter rotating. As the sheath holder 502 extends and retracts, the pins 504a and 504b may slide along the grooves 514a and 514b along the axis A.

In an embodiment, the distance D of the extension or retraction of the sheath holder 502 out of or into the inner cylinder along the axis A may be governed by the length of the grooves 514a and 514b in the sheath holder 502.

In another example, the end 505 of the sheath holder 502 and an introducer coupled to the end 505 may be caused to rotate by rotation the outer cylinder 506. The rotation of the outer cylinder 506 may rotate the pins 504a and 504b which may impart rotational force on the sides of the grooves 514a and 514b in the sheath holder 502, thus rotating the sheath holder 502 about the axis A. Because the outer cylinder 506 and the inner cylinder 510 rotate together through the interaction of the pins 504a and 504b on the grooves 514a and 514b, there is no relative movement between the threads 507 and the threads 512. Therefore, the inner cylinder 510 (and the sheath holder 502) does not extend or retract. In other embodiments, to prevent the rotation of the outer cylinder 506 from causing the sheath holder 502 to be extended and/or retracted based on the rotational engagement of the threads 507 and the threads 512 of the inner cylinder 510, the inner cylinder 510 may be deliberately rotated (for example by rotating shaft 526 to rotate gear 524). In an embodiment, the sheath holder 502 may be rotated any angle R in either direction around the axis A. In other embodiments, the sheath holder 503 may be rotated multiple revolutions around the axis A (e.g., greater than 360 degrees).

Figure 6:
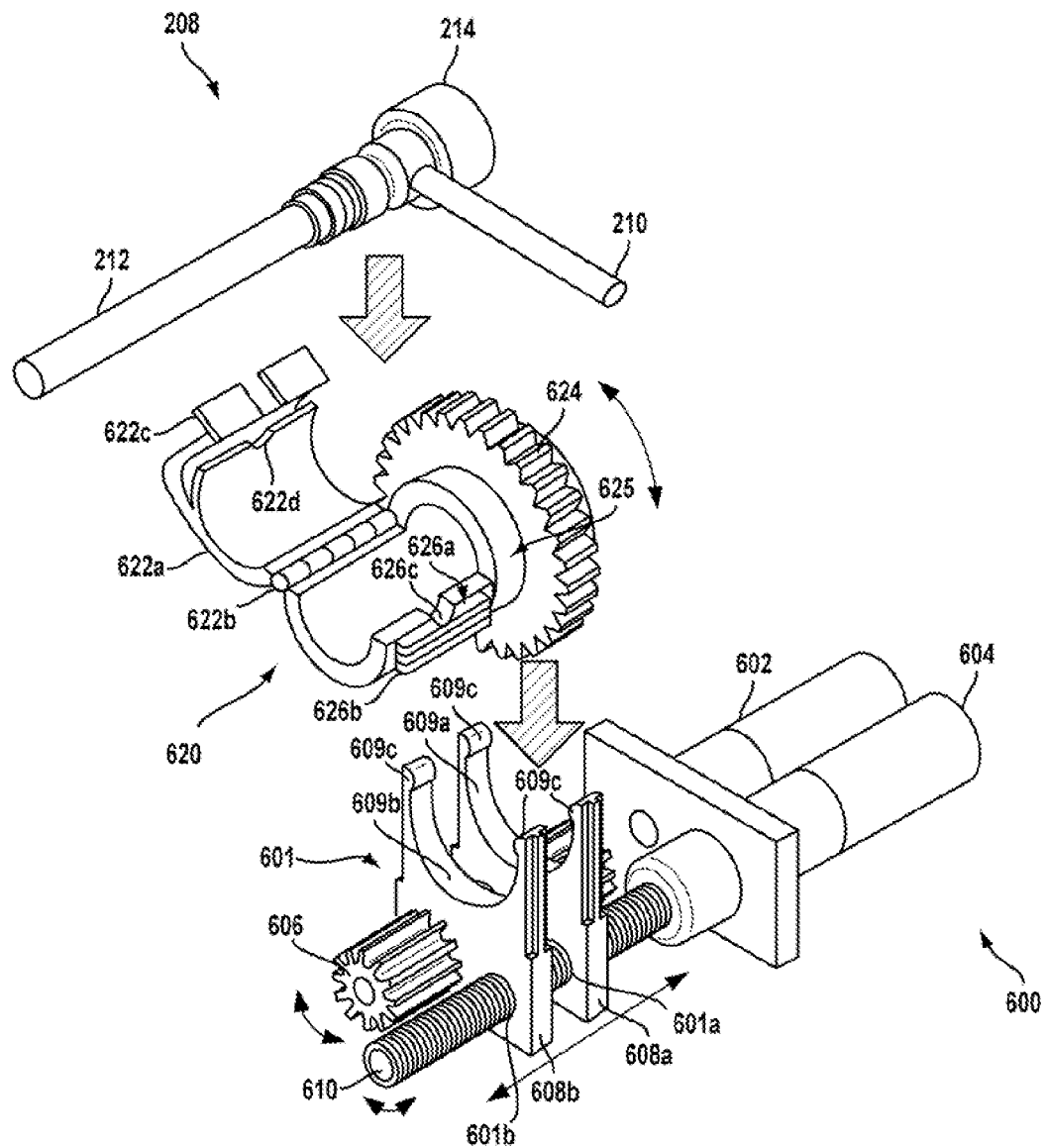
FIG. 6 is a diagram illustrating an oblique view of an embodiment adjustable nose cone with a removable linkage.

FIG. 6 illustrates an embodiment adjustable nose cone 600 with an introducer support 620 that provides an alternative for rotating, extending and retracting an introducer and/or catheter body. The introducer support 620 may comprise a hollow cylinder 625 surrounded by a drive gear 624. The hollow cylinder 625 may extend past the front and back face of the drive gear 624 forming an axle that protrudes from the center of the drive gear 624. The hollow cylinder 625 may include a fixed clasp or clamp receiving portion 626a formed on one end. A clasp or clamp 622a may be rotated in order to couple to the fixed clamp receiving portion 626a by a hinge 622b. The clamp 622a may be secured to the fixed clamp receiving portion 626a by a friction coupling or a clip 622c such that the clamp 622a and fixed clamp receiving portion 626a may form a clamp to securely hold a throat 214 of the introducer 208. In some embodiments, the fixed clamp receiving portion 626a may have a series of teeth 626b that may engage the clip 622c in different positions. The clamp 622a and the fixed clamp receiving portion 626a may thereby be adjusted to provide a secure fit, such as to accommodate different sizes of the throat 214 or to provide different degrees of tightness around the throat 214.

In an embodiment, the clasp 622a and/or fixed clamp receiving portion 626a may each include a gap 622d, 626c to accommodate an irrigation port 210 of the introducer 208. The hollow cylinder 625 may be configured to enable a catheter body to pass through the hollow cylinder 625, such as through a shaft 212 of the introducer 208, which is held in the clamp of the introducer support 620.

The nose cone 600 may further include a guide 601 for receiving the introducer support 620, which may have two supports 608a and 608b. The supports 608a and 608b may include semi-circular linkage supports 609a and 609b, which may be configured to support an outer surface of the hollow cylinder 625 of the introducer support 620 when the introducer support 620 is placed in the nose cone 600. The semicircular linkage supports 609a and 609b may have tabs 609c to provide a secure snap fit coupling for the introducer support 620. The arms of the semicircular linkage supports 609a and 609b may be flexible such that the tabs 609c provide a way of securing the introducer support 620, while allowing easy removal. The supports 608a and 608b may be spaced apart such that the drive gear 624 can rotate between the support 608a and 608b when the hollow cylinder 625 of the introducer support 620 is placed in the supports 608a and 608b.

The nose cone 600 may include a splined shaft 606 driven by motor 602. The splined shaft 606 may pass through openings in the supports 608a and 608b. The introducer support 620 may be supported in the guide 601 such that the teeth of the drive gear 624 may interface with the splines of the splined shaft 606. Rotation of the motor 602 and the splined shaft 606 may engage and rotate the drive gear 624 to rotate the introducer support 620 and the introducer 208.

The guide 601 may be threaded onto a threaded shaft or a worm gear 610 passing through threaded openings 601a and 601b in the supports 608a and 608b. The worm gear 610 may be driven by a motor 604. Rotation of the motor 604 and the worm gear 610 in different directions may cause the guide 601, the introducer support 620 and the introducer 208 to extend and retract.

Activation of the motor 602 to drive the splined shaft 606 may cause the drive gear 624 to rotate, thereby causing the introducer 208 held in the introducer support 620 to rotate allowing rotational positioning of the introducer 208, and a catheter body. Activation of the motor 604 to drive the worm gear 610 may cause the guide 601 to travel along the worm gear 610, thereby causing the introducer 208 held by the removable linkage 602 to extend or retract allowing positioning of the introducer 208 and a catheter body along a linear axis.

In some embodiments, the introducer support 620 and the introducer 208 secured within the introducer support 620 may be removed from the guide 601 by lifting the introducer support 620 out of the guide 601, such as by pulling the introducer support 620 past the tabs 609c. In this manner, the introducer support 620 and introducer 208 may be removed as a single unit, thereby enabling a doctor to manipulate the introducer support 620 and introducer 208 independent of a catheter positioning system.

Figure 7:
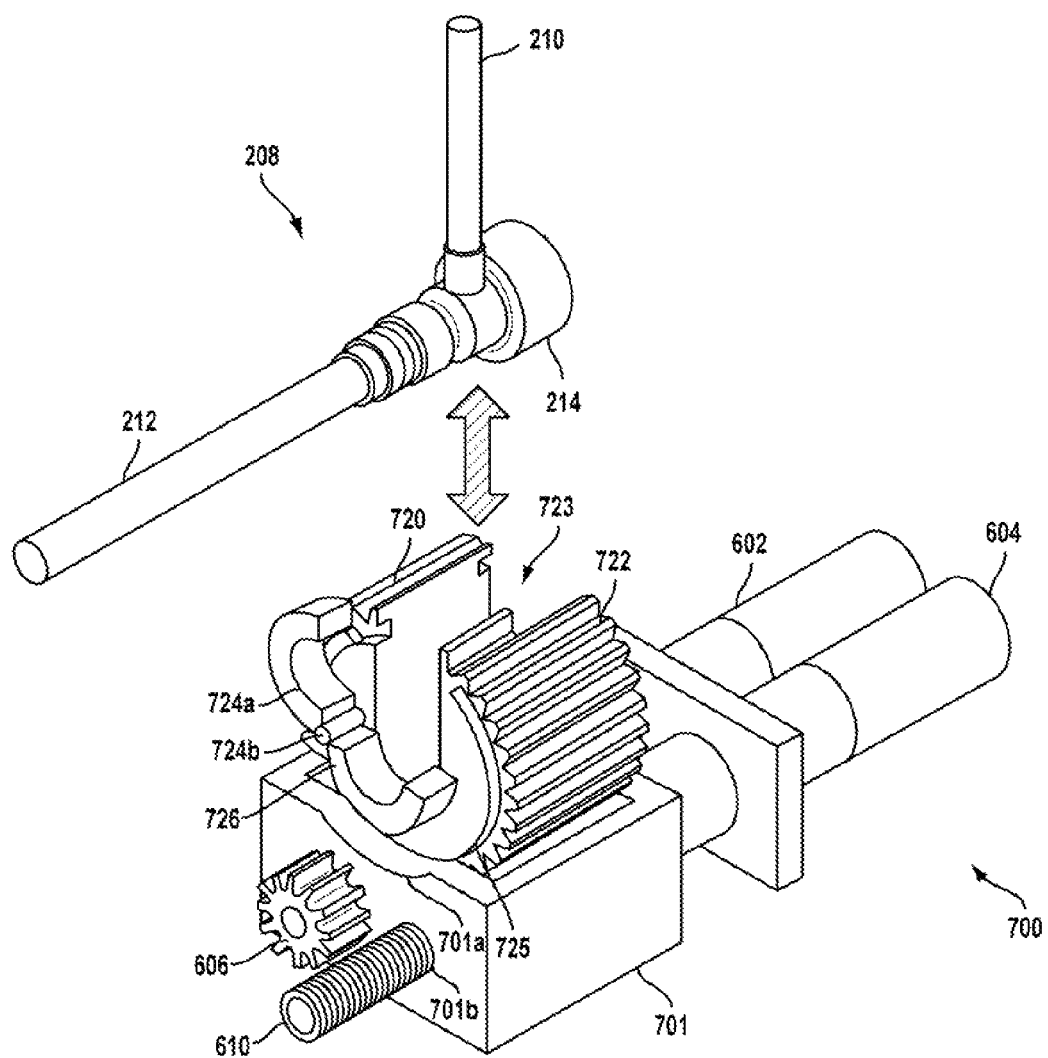
FIG. 7 is a diagram illustrating an oblique view of an alternate embodiment adjustable nose cone with a removable linkage.

FIG. 7 illustrates an alternate embodiment adjustable nose cone 700 similar to nose cone 600 described above with reference to FIG. 6, except that the guide 701 of nose cone 700 may be formed from a single molded piece of material instead of separated supports 608a and 608b. An introducer support 720 may be provided to support the introducer 208. The introducer support 720 may include a drive gear 722 around at least a portion of circumference. For example, the drive gear 722 may be formed in an approximate circular or "U" shape. The drive gear 722 may have a "U" shaped cut out 723 into which the introducer 208 may be inserted. The "U" shaped cut out 723 may extend from the outer surface of the drive gear 722 through the center of the drive gear 722 and the introducer support 720. The bottom of the "U" shaped cut out 723 may be configured to support the throat 214 of the introducer 208. The open top of the "U" shaped cut out 723 may enable the irrigation port 210 to extend out of the drive gear 722 and introducer support 720. Additionally, a ridge 725 may extend from a front face of the drive gear 722 and a ridge may extend from a back face of the drive gear 722 to support the drive gear 722 and the introducer support in the guide 701.

The introducer support 720 may include a fixed clamp portion 726 formed on one end, such as at the bottom of the "U" shaped cut out 723. A movable clamp portion 724a may be configured to rotate about a hinge 724b and couple to the fixed clamp portion 726. The clasp 724 may be secured to the fixed clamp portion 726 by friction or a clip such that the movable clamp portion 724a and fixed clamp portion 726 may form a clamp to hold the throat 214 of the introducer 208 within the "U" shaped cut out 723.

The guide 701 of the nose cone 700 may be configured to support the introducer support 720. As an example the ridge 725 of on the front face of the drive gear 722 and the ridge on the back face of the drive gear 722 may rest in curved cutouts 701a in the walls of the guide 701. The introducer support 720 may be supported in the guide 701 such that the teeth of the drive gear 722 may interface with the splines of the splined shaft 606 that extend through an interior of the guide 701 and are driven by the motor 602. Rotation of the motor 602 and the splined shaft 606 may cause rotation of the drive gear 722 and the introducer support 720, and in turn may cause rotation of the introducer 208. The guide 701 may further be coupled to the worm gear 610 through a threaded opening 701b that extends through the guide 701. The worm gear may be rotated by the motor 604. Rotation of the motor 604 and the worm gear 610 may cause linear movement of the guide 701 and corresponding linear movement to extend or retract the introducer support 720 and the introducer 208.

Figure 8A:
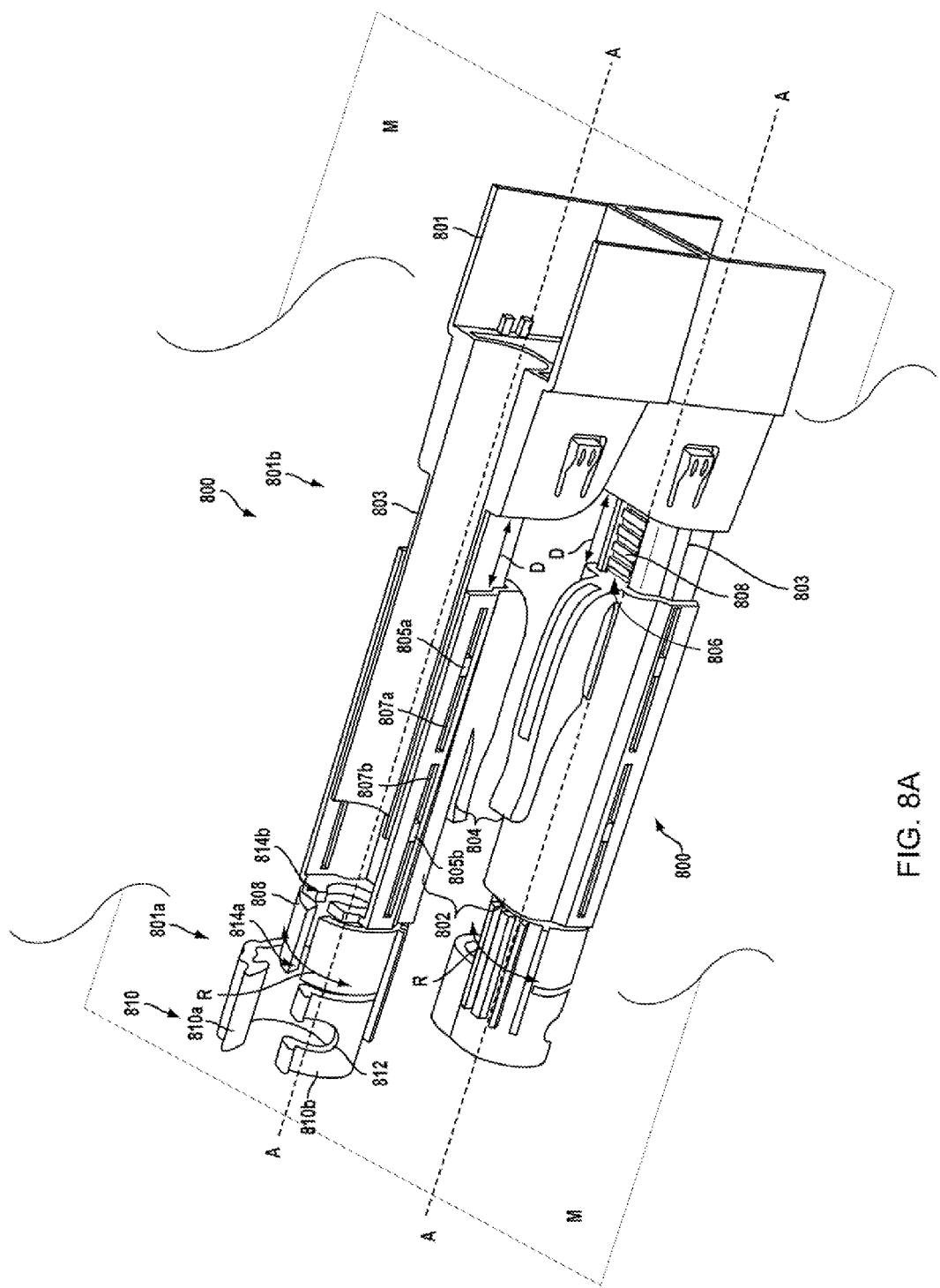
FIG. 8A is a diagram illustrating an oblique view of an alternate embodiment adjustable nose cone and a reflection of the underside of the adjustable nose cone.
Figure 8B:
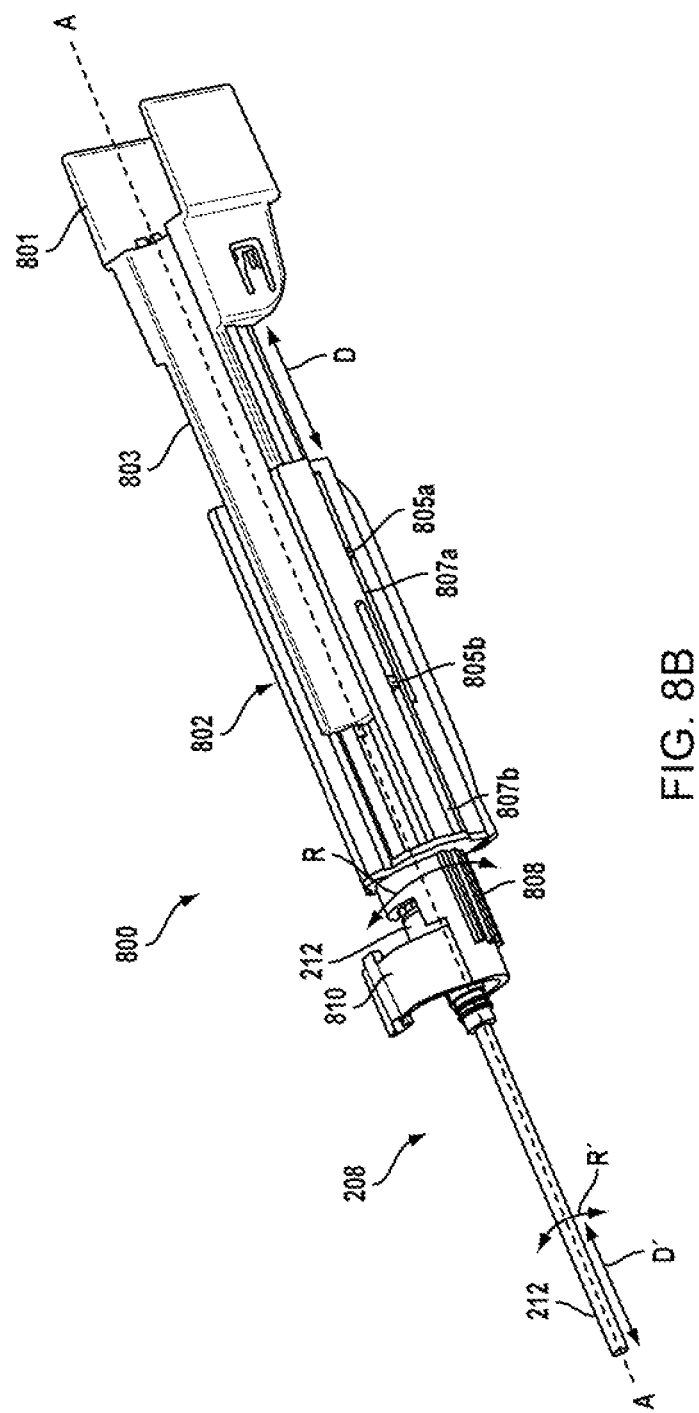
FIG. 8B is a diagram illustrating another oblique view of the adjustable nose cone of FIG. 8A.

FIG. 8A and FIG. 8B illustrate two views of another embodiment adjustable nose cone 800. The embodiment nose cone 800 may be adjustable to enable the introducer 208 to be rotated through an angle R' around an axis A and/or to be extended or retracted a distance D' along the axis A.

FIG. 8A presents a top perspective view of the nose cone 800 and a reflection showing a bottom perspective view of the nose cone 800 in a mirrored plane M. FIG. 8A illustrates the relationship of components on the top of the nose cone 800 and the underside of the nose cone 800. The nose cone 800 may include a support portion 801, a slide portion 802, and a hollow rotating portion 808. A first or proximal end 801a of the support portion 801 may be configured to connect the nose cone 800 to a catheter positioning system, for example via snaps, clamps, and/or a friction connector. A second or distal end 801b of the support portion 801 may be configured to form a slide arm 803 extending along the axis A. The slide arm 803 may include one or more tabs 805a, 805b configured to fit within and travel along longitudinal slots 807a, 807b formed in a surface of the slide portion 802. The tabs 805a and 805b may secure the slide arm 803 to the slide portion 802. The tabs 805a and 805b may further help to ensure proper alignment when the slide arm 803 is extended and retracted relative to the slide portion 802. The longitudinal slots 807a, 807b may have a length configured so that the one or more tabs 805a, 805b contact an end of the corresponding slot at a maximum extension distance D. The end of the slots 807a and 807b may act as mechanical stops by preventing the slide arm 803 from disconnecting from slide portion 802, such as when fully extended or fully retracted.

In an embodiment, the support portion 801 and slide portion 802 may be configured to hold together at an established fixed extension distance D. The slide portion 802 may be slidably attached to the slide arm 803 and may be configured to slide over the slide arm 803 to extend or retract a distance D along the slide arm 803 and axis A. For example, a latching lever 804 may be provided on the slide portion 802. The latching lever 804 may operate to engage and disengage a tooth 806 from ribs 808 (shown in the reflection) formed in the bottom surface of the slide arm 803. The engagement of the tooth 806 of the latching lever 804 with the one or more ribs 808 of the slide arm 803 may "lock" the slide portion 802 into a given position and may prevent the slide portion 802 from further extending or retracting along the slide arm 803 and axis A. The latching lever 804 may be depressed to disengage the tooth 806 from the one or more ribs 803 to enable the slide portion 802 to slide over the slide arm 803 to extend or retract a distance D along the slide arm 803 and axis A. In some embodiments, the latching lever 804 may be manually operated. In other embodiments, it may be possible for the latching lever 804 to be operated automatically by pressure from an external mechanism (not shown).

The rotating portion 808 may be rotationally coupled to the slide portion 802 and configured to rotate through an angle R around the axis A. An end of the rotating portion 808 opposite the slide portion 802 may include an introducer clamp 810 formed from a fixed clamp portion 810b and a clamp tab 810a which may be coupled to the fixed clamp portion 810b by rotating about a hinge (not shown). Alternatively, the clamp tab 810a may be made from a flexible material that is self-hinging or that may have a crease hinge or other type of hinge. The clamp tab 810a may fasten to the fixed clamp portion 810b by a friction connection, snap fit connection, interlocking tabs, and so on. The introducer clamp 810 may fasten over a throat 214 of an introducer 208 to securely hold the introducer 208 in place.

In an embodiment, the introducer clamp 810 may include one or more cutout 812 configured to enable the irrigation port 210 of the introducer to pass through the fixed clamp portion 810b and clamp tab 810a of the introducer clamp 810. While the cutout 812 is shown in the fixed clamp portion 810b, a cutout 812 may alternatively be provided in the clamp tab 810a, or may be provided in both the clamp tab 810a and the fixed clamp portion 810b.

In the illustrated embodiment, the slide portion 802 and slide arm 803 may be formed as open troughs enabling direct access to the inner portions of the slide portion 802 and slide arm 803 from one or more sides of the slide portion 802 and slide arm 803, such as for placement of an introducer, catheter, or other component therein. In some embodiments, an introducer and catheter body or other components may be threaded through the rotating portion 808. In an optional embodiment, the rotating portion 808 may include a slot 814a and the slide portion 802 may include a slot 814b such that an introducer, catheter body or other components may be inserted from the top without threading. The rotating portion 808 may be rotated around the axis A to align the slot 814a with the slot 814b, thereby enabling the body of a catheter to be inserted from above such as by passing through the outer surface of the rotating portion 808 and into the center of the rotating portion 808 and the center of the troughs of the slide portion 802 and slide arm 803.

FIG. 8B illustrates another view of the nose cone 800 with the introducer 208 placed in the introducer clamp 810 of the rotating portion 808. A catheter body may pass through the slide arm 803, the slide portion 802, the rotating portion 808, the clamp 810, and the introducer 208, such as when the components of the nose cone 800 and introducer 208 are coupled together.

In an embodiment, the rotating portion 808 may be rotated through an angle R around the axis A causing a corresponding rotation to be imparted to the shaft 212 of the introducer 208. The shaft 212 may thereby be rotated a distance R in a direction R' around the axis A.

By providing a sliding connection between the slide portion 802 and the slide arm 803, the shaft 212 of the introducer 208 can be extended or retracted. For example, the shaft 212 may be extended or retracted a distance D' along the axis A by sliding the slide portion 802 a distance D along the slide arm 803. In this manner, the nose cone 800 may be extended, retracted and rotated to various angles. The nose cone 800 may be repositioned relative to the patient (and/or moved into and out of the patient) over a range of distances to direct the shaft 212 of the introducer 208 and/or a shaft of a catheter passed through the nose cone 800 and introducer 208 in a particular direction and/or to a particular spot within the patient.

As described above, the programmable control system 132 may be configured with processor-executable instructions to issue drive or power commands to each of the motors in the catheter positioning system, including the drive motors within or coupled to the introducer or introducer support, such as a motor coupled to the shafts 516, 526 extending from and driving the gears 514, 524 described above with reference to FIG. 5C, the motors 602, 604 driving the splined shaft 606 and the worm gear 610, described above with reference to FIG. 6 and FIG. 7, and so on.

Those skilled in the art will recognize that the methods and systems of the present invention have many applications, may be implemented in many manners and, as such, is not to be limited by the preceding exemplary embodiments and examples. Additionally, the functionality of the components of the preceding embodiments may be implemented in different manners. Further, it is to be understood that the steps in the embodiments may be performed in any suitable order, combined into fewer steps or divided into more steps. Thus, the scope of the present invention covers conventionally known and future developed variations and modifications to the system components described herein, as would be understood by those skilled in the art.

What is claimed is:

1. A nose cone configured for supporting an introducer for a catheter positioning system, comprising:
   a support portion including a slide arm;
   a slide portion configured to slide over a surface of the slide arm to extend along an axis of the nose cone, wherein the surface of the slide arm includes one or more ribs and the slide portion includes a lever having a tooth configured to engage with the one or more ribs to prevent the slide arm from extending along the axis of the nose cone; and
   a hollow rotating portion rotationally coupled to the slide portion, an end of the hollow rotating portion comprising a clamp configured to hold the introducer for the catheter positioning system, wherein the hollow rotating portion is configured to rotate the clamp around the axis of the nose cone.

2. The nose cone of claim 1, wherein the clamp includes a cutout configured to accommodate an irrigation port of the introducer.

3. The nose cone of claim 1, wherein:
the slide arm and the slide portion are each formed as troughs to accept a catheter; and
the slide portion and the hollow rotating portion each include slots that when aligned enable a catheter body to pass through an outer surface of the hollow rotating portion into a center of the hollow rotating portion, the slide portion, and the slide arm.

4. The nose cone of claim 1, further comprising:
at least one longitudinal slot extending along a length of the slide portion; and
at least one tab on the support portion configured to travel in the at least one longitudinal slot of the slide portion.

\* \* \* \* \*